(12) United States Patent
Lim

(10) Patent No.: US 7,927,356 B2
(45) Date of Patent: Apr. 19, 2011

(54) DYNAMIC CONSTRUCTS FOR SPINAL STABILIZATION

(75) Inventor: Roy Lim, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 485 days.

(21) Appl. No.: 11/483,330

(22) Filed: Jul. 7, 2006

(65) Prior Publication Data

US 2008/0021459 A1 Jan. 24, 2008

(51) Int. Cl.
*A61B 17/58* (2006.01)
*A61B 17/66* (2006.01)
*A61B 17/70* (2006.01)
*A61B 17/88* (2006.01)

(52) U.S. Cl. ........................................ 606/257; 606/264

(58) Field of Classification Search ............... 606/60, 606/246–267, 269, 279, 300, 86 R, 90, 105; 623/17.11
See application file for complete search history.

(56) References Cited

U.S. PATENT DOCUMENTS

| | | | |
|---|---|---|---|
| 5,486,174 A * | 1/1996 | Fournet-Fayard et al. ... | 606/261 |
| 5,540,688 A | 7/1996 | Navas | |
| 5,562,660 A * | 10/1996 | Grob ............................. | 606/258 |
| 7,329,258 B2 * | 2/2008 | Studer ........................... | 606/250 |
| 7,377,921 B2 * | 5/2008 | Studer et al. .................. | 606/248 |
| 2002/0035366 A1 * | 3/2002 | Walder et al. ................. | 606/61 |
| 2002/0133155 A1 | 9/2002 | Ferree | |
| 2003/0171749 A1 | 9/2003 | LeCouedic et al. | |
| 2004/0002708 A1 | 1/2004 | Ritland | |
| 2004/0049189 A1 | 3/2004 | LeCouedic et al. | |
| 2004/0049190 A1 * | 3/2004 | Biedermann et al. ......... | 606/61 |
| 2004/0073215 A1 | 4/2004 | Carli | |
| 2004/0143264 A1 | 7/2004 | McAfee | |
| 2005/0010220 A1 * | 1/2005 | Casutt et al. .................. | 606/61 |
| 2005/0131407 A1 | 6/2005 | Sicvol et al. | |
| 2005/0182401 A1 * | 8/2005 | Timm et al. ................... | 606/61 |
| 2005/0203514 A1 | 9/2005 | Jahng et al. | |
| 2005/0203519 A1 | 9/2005 | Harms et al. | |
| 2005/0261685 A1 | 11/2005 | Fortin et al. | |
| 2005/0288672 A1 | 12/2005 | Ferree | |
| 2006/0009768 A1 | 1/2006 | Ritland | |
| 2006/0036240 A1 | 2/2006 | Colleran et al. | |
| 2006/0084994 A1 | 4/2006 | Atkinson et al. | |
| 2006/0106381 A1 | 5/2006 | Ferree et al. | |
| 2006/0149242 A1 * | 7/2006 | Kraus et al. ................... | 606/61 |
| 2006/0195090 A1 * | 8/2006 | Suddaby ........................ | 606/61 |
| 2007/0049937 A1 * | 3/2007 | Matthis et al. ................ | 606/61 |
| 2007/0161994 A1 * | 7/2007 | Lowery et al. ................ | 606/61 |
| 2007/0198014 A1 * | 8/2007 | Graf et al. ..................... | 606/61 |
| 2007/0233075 A1 * | 10/2007 | Dawson ........................ | 606/61 |
| 2007/0233085 A1 * | 10/2007 | Biedermann et al. ......... | 606/61 |
| 2007/0270814 A1 * | 11/2007 | Lim et al. ...................... | 606/61 |
| 2008/0183214 A1 * | 7/2008 | Copp et al. .................... | 606/265 |

FOREIGN PATENT DOCUMENTS

EP 1 388 323 A1 2/2004
WO WO 01/45576 A1 6/2001

* cited by examiner

*Primary Examiner* — Eduardo C Robert
*Assistant Examiner* — Sameh Boles

(57) ABSTRACT

Devices and methods for spinal stabilization include first and second anchors engageable to respective ones of first and second vertebrae and a connector assembly engageable with the anchors to provide a desired stabilization effect. The connector assembly can include a connecting element and a bumper element engageable to the first and second anchors.

17 Claims, 6 Drawing Sheets

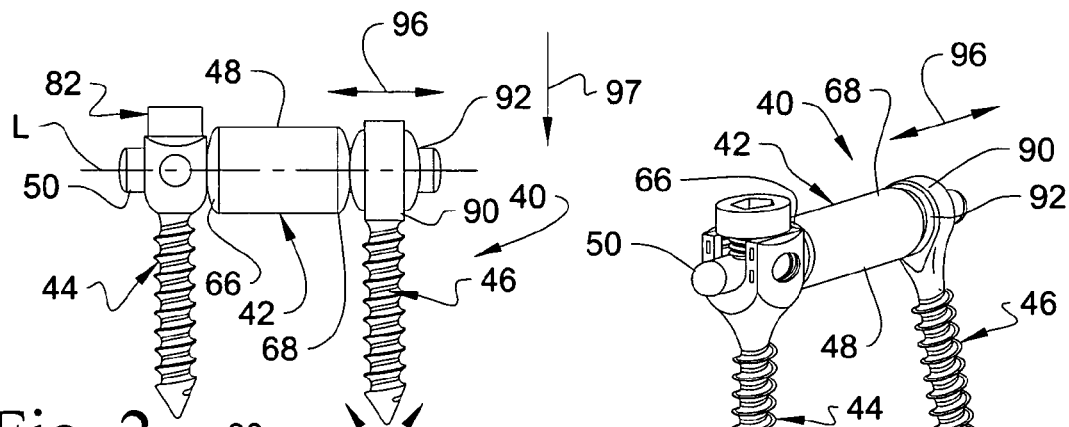
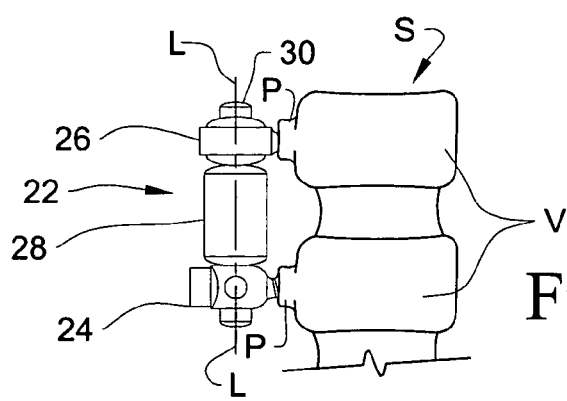
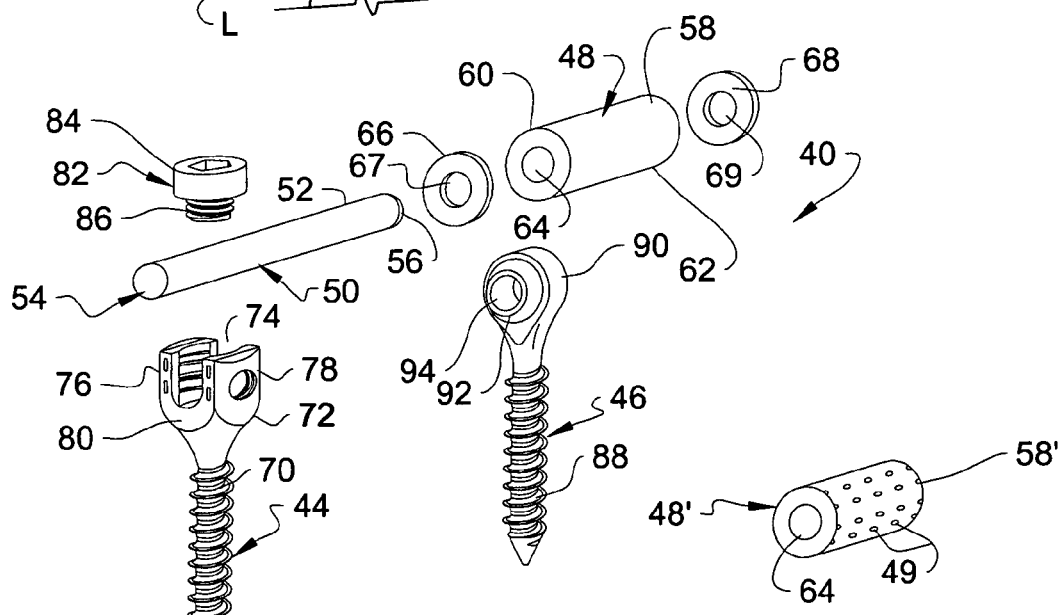

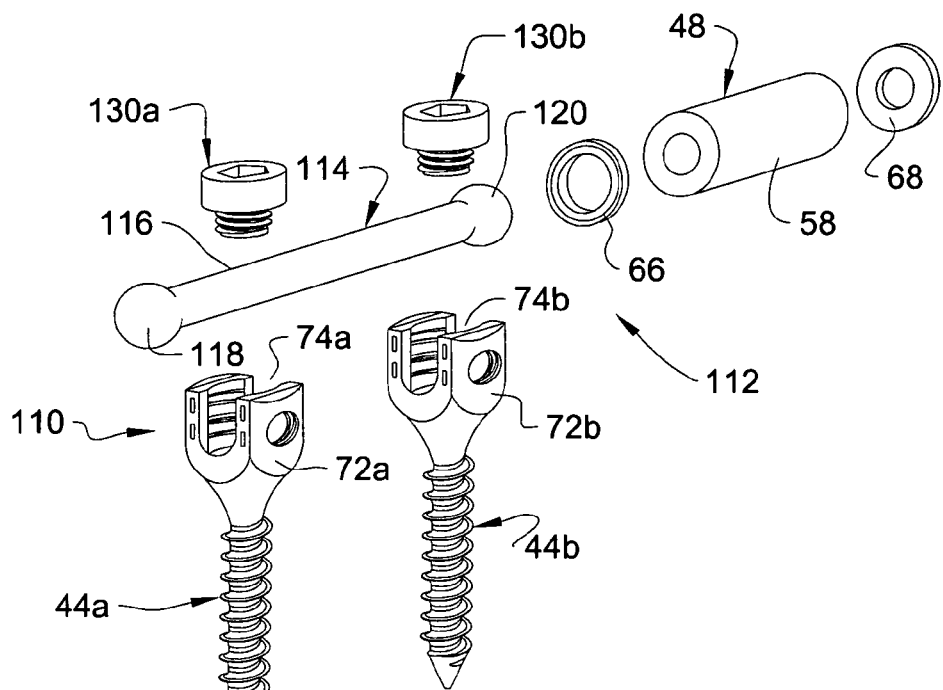
Fig. 7
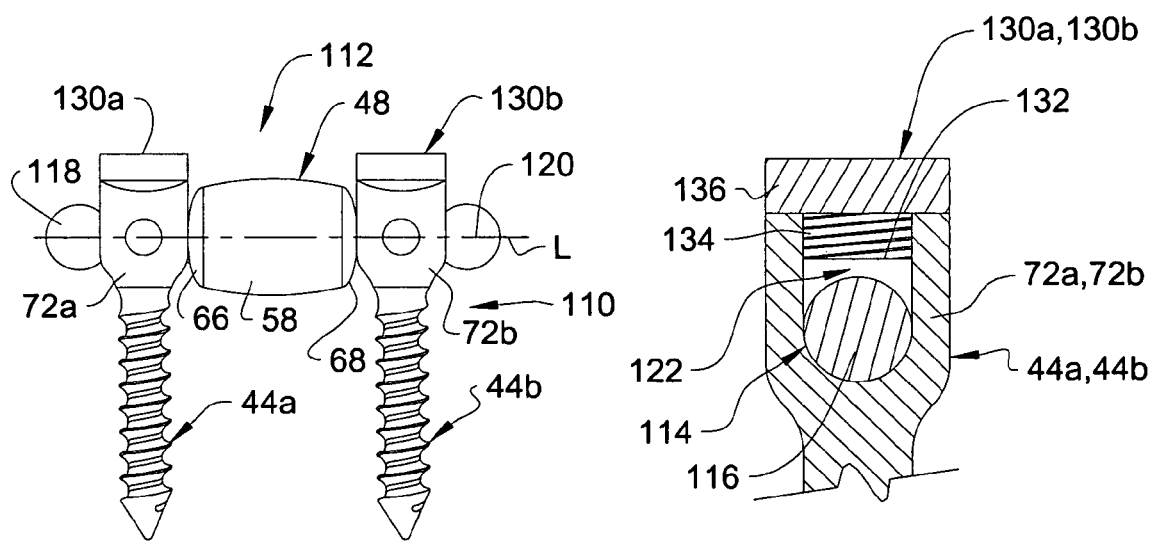
Fig. 6
Fig. 8

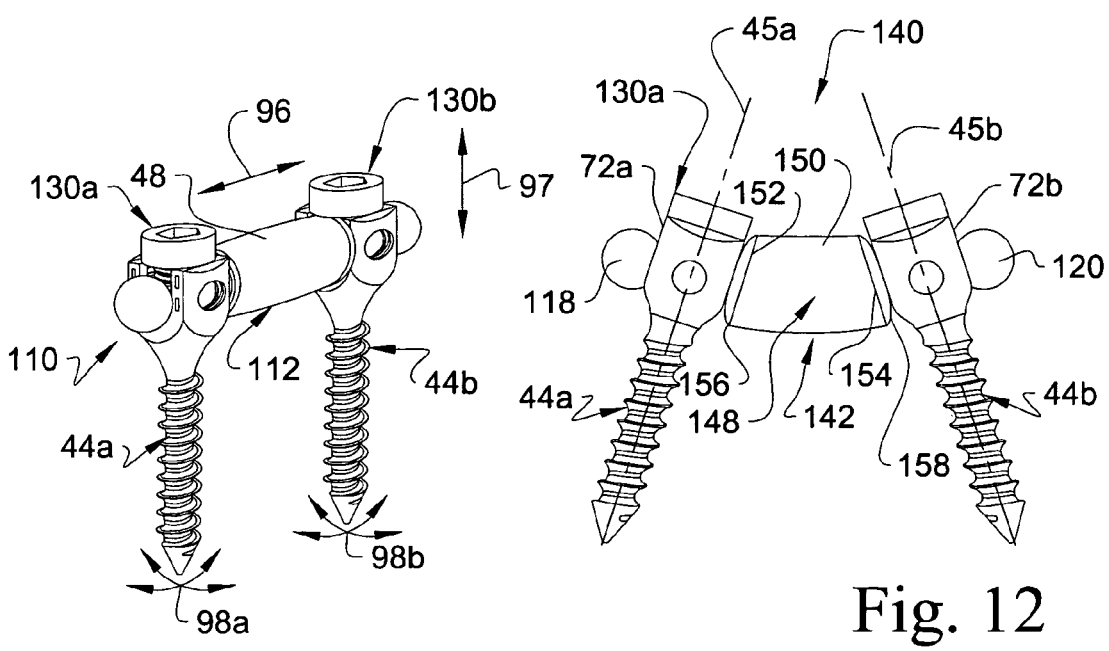
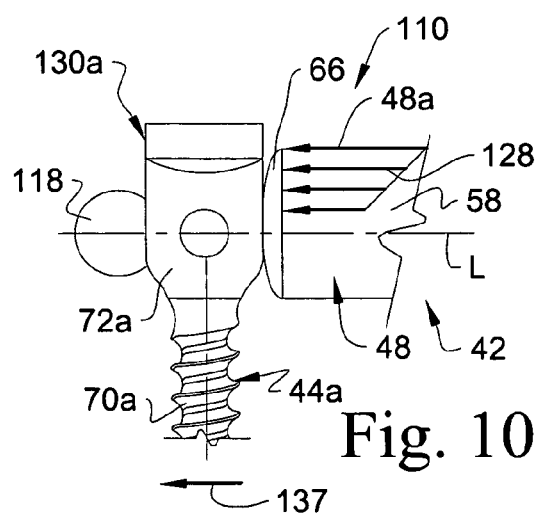
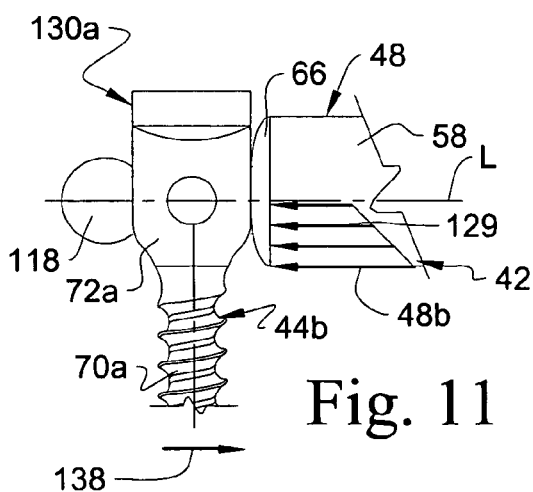

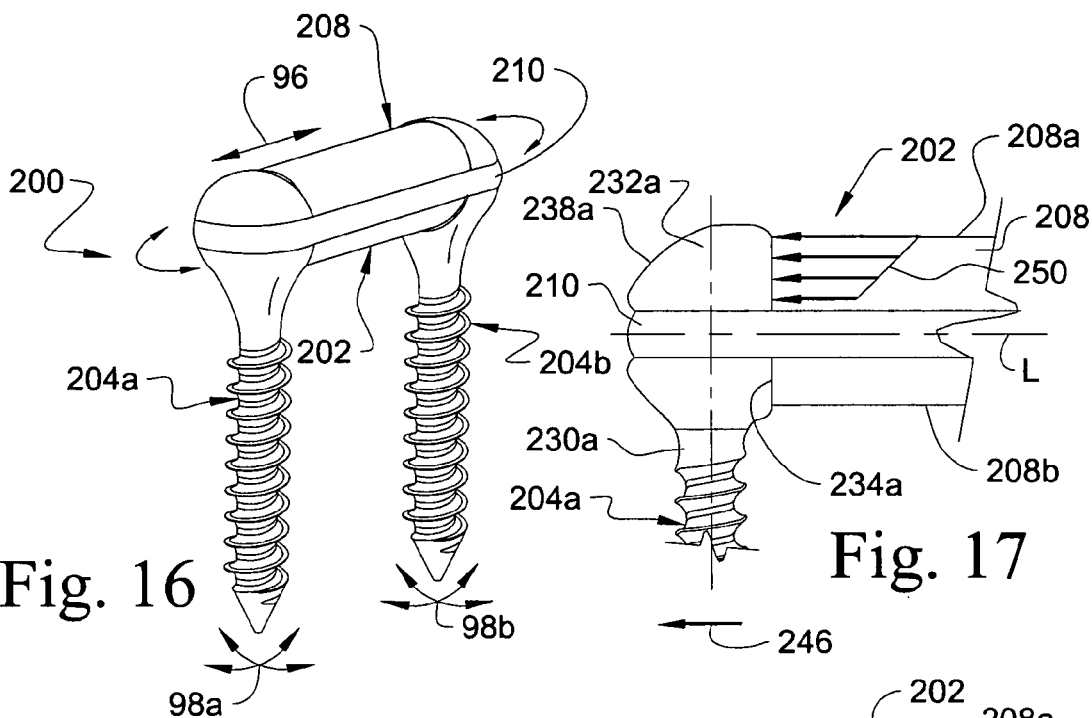
Fig. 16
Fig. 17
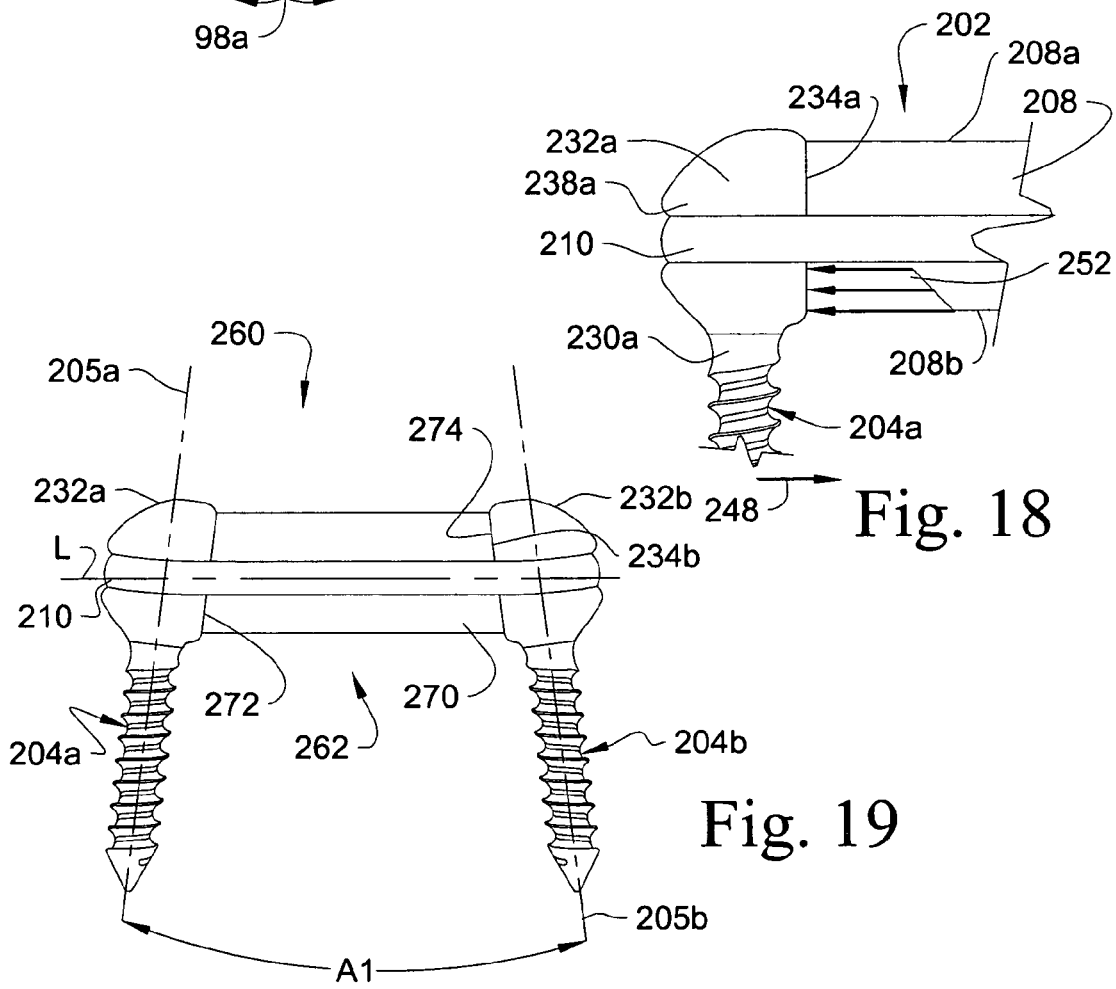
Fig. 18
Fig. 19

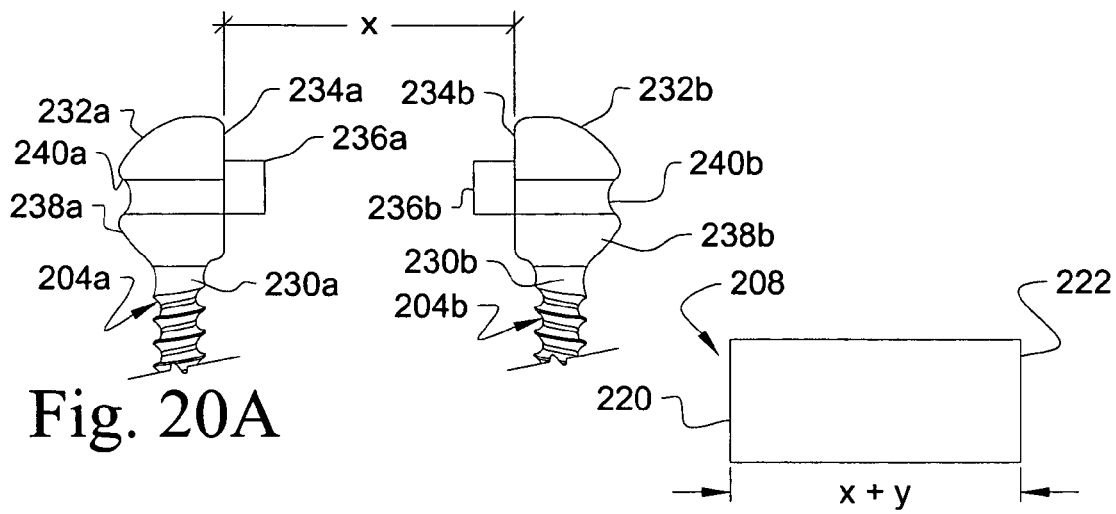
Fig. 20A
Fig. 20B
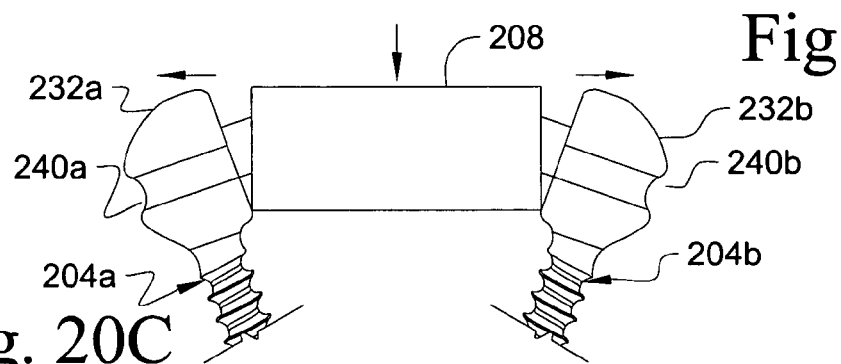
Fig. 20C
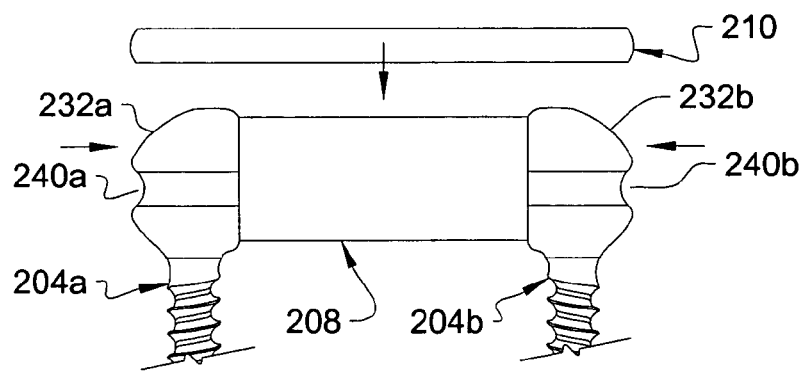
Fig. 20D
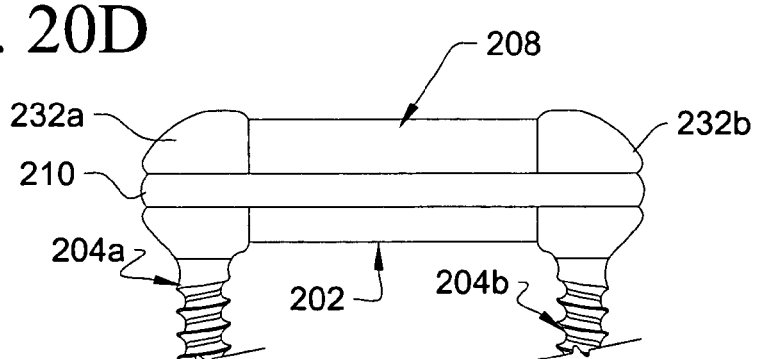
Fig. 20E

DYNAMIC CONSTRUCTS FOR SPINAL STABILIZATION

BACKGROUND

Elongated connecting elements, such as rods, plates, tethers, wires, cables, and other devices have been implanted along the spinal column and connected between two or more anchors engaged between one or more spinal motion segments. Such connecting elements can provide a rigid construct that resists movement of the spinal motion segment in response to spinal loading or movement of the spinal motion segment by the patient. Still other connecting elements are flexible to permit at least limited spinal motion while providing resistance to loading and motion of the spinal motion segment. Such flexible connecting elements can be considered to provide dynamic spinal stabilization since at least limited movement of the spinal motion segment is preserved after implantation of the connecting element.

While prior connecting elements provide various spinal stabilization options, there remains a need for stabilization constructs that can provide dynamic resistance to forces and permit motion of the spinal column segment in different directions while maintaining stabilization of the spinal column segment and the structural integrity of the construct.

SUMMARY

The present invention generally relates to constructs and methods for dynamically stabilizing a spinal column motion segment including at least two vertebrae by engaging the construct between the at least two vertebrae. The construct can be engaged to at least two anchors engaged to respective ones of the at least two vertebrae while permitting motion of the vertebrae relative to one another. The construct includes a bumper element extending between the anchors to resist movement of the anchors toward one another and a connecting element extending between the anchors to axially link the anchors to one another.

According to one aspect, a spinal stabilization construct includes first and second anchors each including a proximal head and a distal portion engageable to respective ones of first and second vertebral bodies. The construct also includes a connector assembly extending along a longitudinal axis between the proximal heads of the first and second anchors. The connector assembly includes an elongated connecting element with a rigid body extending between opposites ends that are located in passages of respective ones of the proximal heads. The connector assembly also includes a flexible bumper element positioned about the connecting element with the bumper element extending between opposite ends in abutting engagement with the proximal heads to resist movement of the heads toward one another. The connector assembly also includes an engagement member coupled to the proximal head of the first anchor. The engagement member secures the respective opposite end of the connecting element in the passage of the proximal head of the first anchor. The other of the opposite ends of the connecting element is captured in the passage of the proximal head of the second anchor and is configured with the proximal head to move along the longitudinal axis relative to the second anchor in response to movement of the first and second vertebrae along the longitudinal axis.

In another aspect, a spinal stabilization construct includes first and second anchors that each include a proximal head and a distal portion engageable to respective ones of first and second vertebral bodies. The construct also includes a connector assembly extending along a longitudinal axis between the proximal heads of the first and second anchors. The connecting assembly includes a bumper element extending along the longitudinal axis and positioned between the proximal heads in abutting engagement with the proximal heads to resist movement of the heads toward one another and an elongated connecting element including a band-shaped body extending along the longitudinal axis and around the proximal heads of the first and second anchors.

In yet another aspect, a method for assembling a spinal stabilization construct comprises: engaging a first anchor to a first vertebra; engaging a second anchor to a second vertebra; measuring a distance between adjacent inner surfaces of proximal heads of the first and second anchors; selecting a bumper element having a length between opposite ends thereof greater than the distance measured; distracting the first and second anchors to separate the proximal heads; positioning the bumper element between the inner surfaces of the proximal heads; and compressing the proximal heads to secure the bumper element between the inner surfaces.

In another aspect, a method for assembling a spinal stabilization construct comprises: engaging a first anchor to a first vertebra; engaging a second anchor to a second vertebra; positioning a bumper element around an elongated connecting element; engaging a first end of the connecting element to the first anchor; and slidably capturing the second end of the connecting element in the second anchor with the bumper element extending between the first and second anchors.

According to another aspect, a spinal stabilization construct comprises first and second bone anchors and an elongated connecting element extending between the first and second bone anchors and a bumper element positioned around the connecting element between the first and second anchors. The connecting element includes a first end extending from the bumper element fixedly engaged with the first anchor and a second end extending from the bumper element movably engaged with the second bone anchor so that the second bone anchor is movable to translate along the connecting element and pivotal about the connecting element.

In a further aspect, a spinal stabilization construct comprises first and second bone anchors and an elongated connecting element extending between the first and second bone anchors and a bumper element positioned around the connecting element between the first and second anchors. The connecting element includes a first end extending from the bumper element captured in the first bone anchor and a second end extending from the bumper element captured in the second bone anchor. Each of the first and second bone anchors are movable relative to the connecting element to translate along the connecting element and pivot about the connecting element.

In another aspect, a spinal stabilization construct comprises first and second bone anchors and an elongated bumper element positioned between and abuttingly engaging the first and second bone anchors. The construct further comprises an elongated connecting element forming a band extending around the first and second anchors and along opposite sides of the bumper element.

These and other aspects will be discussed further below.

BRIEF DESCRIPTION OF THE DRAWINGS

FIG. 1 is a side view of a spinal column segment with a dynamic stabilization construct secured thereto.

FIG. 2 is an elevation view of one embodiment of the stabilization construct of FIG. 1.

FIG. 3 is a perspective view of the stabilization construct of FIG. 2.

FIG. 4 is an exploded view of the stabilization construct of FIG. 2.

FIG. 5 is a perspective view of another embodiment bumper element useable with the stabilization construct of FIG. 2.

FIG. 6 is an elevation view of another embodiment of the dynamic stabilization construct of FIG. 1.

FIG. 7 is an exploded perspective view of the stabilization construct of FIG. 6.

FIG. 8 is a sectional view showing a connecting element of the stabilization construct engaged to a bone anchor.

FIG. 9 is a perspective view of the stabilization construct of FIG. 6.

FIG. 10 is an elevation view of a portion of the stabilization construct of FIG. 6 showing a first load distribution pattern.

FIG. 11 is an elevation view of a portion of the stabilization construct of FIG. 6 showing a second load distribution pattern.

FIG. 12 is an elevation view showing a lordotic version of the stabilization construct of FIG. 6.

FIG. 16 is a perspective view of the stabilization construct of FIG. 14.

FIG. 17 is an elevation view of a portion of the stabilization construct of FIG. 14 showing a first load distribution pattern.

FIG. 18 is an elevation view of a portion of the stabilization construct of FIG. 14 showing a second load distribution pattern.

FIG. 19 is an elevation view showing a lordotic version of the stabilization construct of FIG. 14.

FIGS. 20A-20E show various steps of a method for assembling the stabilization construct of FIG. 14.

DESCRIPTION OF THE ILLUSTRATED EMBODIMENTS

Figure 13:
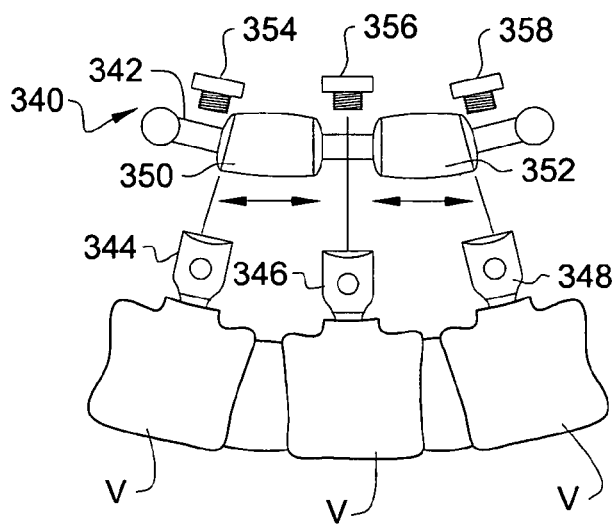
FIG. 13 is an exploded elevation view of a spinal column segment and a multi-level embodiment of the dynamic stabilization construct of FIG. 6.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Constructs and methods for providing dynamic stabilization of one or more spinal motion segments are provided. The constructs and methods include a connector assembly between two or more bone anchors that can be engaged to respective ones of at least two or more vertebral bodies of a spinal motion segment. The connector assembly extends along a longitudinal axis and includes a bumper element extending between the bone anchors to dynamically resist movement of the anchors toward one another and a connecting element that axially couples the anchors to one another.

In one embodiment, one end of the connecting element is captured in at least one of the bone anchors with at least axial movement of the connecting element relative to the bone anchor permitted. In one form, the other end of the connecting element is fixed in the other bone anchor. In another form, the other end of the connecting element is captured in and can axially move in the other bone anchor. In another embodiment, the connecting element includes a band that extends around the bone anchors to axially limit or prevent the anchors from movement away from one another.

In one embodiment, the connecting element can extend through the bumper element for engagement to the first and second bone anchors. In one form, the bone anchor includes a head with a pivoting ball arrangement through which an end of the connecting element extends. In another form, the ends of the connection element are slidably captured in heads of each of the bone anchors and extend to enlarged end elements that contact the respective bone anchor heads to limit movement of the bone anchors away from one another. In another embodiment, the connecting element extends around the bumper element. In one form, the bone anchors can include heads with flattened inner surfaces in abutting engagement with a respective end of the bumper element. In a further form, the outer perimeter of the heads of the bumper assembly can include a groove to receive the connecting element therein so that the connecting element extends around at least a portion of each of the bone anchor heads.

The bone anchors discussed herein can be multi-axial or uni-axial in form, and can include an anchor member engageable to a vertebral body and a proximal head for receiving or engaging a respective end of the connector assembly. The multi-axial anchors allow the anchor member to be positioned at various angles relative to the head of the anchor. The uni-axial anchors can also provide a fixed positioning of the connector assembly to the bone anchor. The anchor member of the bone anchors can form a distal lower portion that is engageable to a vertebral body with the proximal head positioned adjacent the vertebral body. In one embodiment, the anchor member is in the form of a bone screw with a threaded shaft and a proximal head that is pivotally captured in the receiver. In other embodiments, the distal anchor member can be in the form of a hook, staple, cable, tether, suture anchor, interbody fusion implant, artificial disc implant, bolt, or other structure engageable to bony tissue. The proximal head can include a receiver with a U-shape, O-shape, or other shape that defines a passage that receives or engages the respective end of the connector assembly therein, thereon, therethrough, or thereover, for example. The connector assembly can extend from one or both of the bone anchors for securement to one or more additional vertebral bodies in multi-level stabilization constructs.

FIG. 1 illustrates a dynamic stabilization construct 20 engaged along a spinal column of a patient. More specifically, stabilization construct 20 can be affixed to pedicles P of vertebrae V of the spinal column segment S from a posterior approach. Also contemplated are applications in posterior-lateral, lateral, antero-lateral and anterior approaches, and applications where the stabilization construct 20 is engaged to other portions of the vertebrae V, such as the anterior body portion or any of the posterior elements. The spinal column segment S can comprise two vertebrae V as shown for a single level stabilization procedure or three or more vertebrae in multi-level stabilization procedures. The vertebrae V can be any one or combination of the sacral, lumbar, thoracic, and cervical vertebrae of the spinal column.

Stabilization construct 20 can include a connector assembly 22 extending along a longitudinal axis L between first bone anchor 24 and second bone anchor 26. Connector assembly 22 can include a bumper element 28 positioned between bone anchors 24, 26 and in contact therewith to dynamically resist movement of bone anchors 24, 26 toward one another. Connector assembly 22 can also include connecting element 30 extending along axis L and axially linking or connecting anchors 24, 26 to one another. Connecting element 30 can be engaged, captured or constrained with anchors 24, 26 to couple connector assembly 22 to anchors 24, 26. Connector assembly 22 can include an overall length along longitudinal axis L sized to extend between bone anchors 24, 26 when engaged to at least two vertebral bodies V. Connector assembly 22 can also be provided with a length sized to extend along three or more vertebrae with at least one bumper element between at least two adjacent vertebrae. The portions of the connector assembly 22 extending between the other vertebrae may include a bumper element, or may include a rod portion between the other vertebrae that provides rigid or dynamic stabilization without a bumper element.

In stabilization construct 20, bone anchors 24, 26 are affixed to various locations of the spinal column segment S, such as the pedicles P, and interconnected with one or more connector assemblies 22. Other procedures contemplate connector assemblies 22 may be employed at other locations about the spinal column, including anterior, antero-lateral, and lateral locations. Stabilization construct 20 may also be employed in procedures where such locations are combined; e.g. to provide posterior and anterior stabilization. Stabilization construct 20 may be used for, but is not limited to, treatment of degenerative spondylolisthesis, herniation, degeneration, arthritis, fracture, dislocation, scoliosis, kyphosis, spinal tumor, and/or a failed previous fusion.

FIGS. 2-4 show various views of one embodiment of stabilization construct 20 designated as stabilization construct 40. Stabilization construct 40 includes a connector assembly 42 extending between and engageable to a first anchor 44 and a second anchor 46. Connector assembly 42 includes a bumper element 48 positioned between and abuttingly engaging anchors 44, 46 and a connecting element 50 extending between and engaged to anchors 44, 46. Bumper element 48 and connecting element 50 extend along longitudinal axis L.

Connecting element 50 includes an elongated rod-like body 52 extending between a first end 54 and an opposite second end 56. Body 52 can have a circular cross-section as shown, or can include any other cross-sectional shape. The cross-section can further be constant along the length of body 52 or be varying in size and shape. Body 52 can be rigid so that when subjected to forces from spinal column loading it retains its shape and length.

Bumper element 48 includes an elongated cylindrical body 58 extending between a first end 60 and an opposite second end 62 along longitudinal axis L. Body 58 can define a central passage 64 sized and shaped to receive connecting element 50 therethrough with ends 54, 56 extending axially from ends 60, 62, respectively. Cylindrical body 58 and passage 64 can each define a circular cross-section as shown, or one or both may include any suitable non-circular cross-sectional shape along all or a portion of the length thereof.

Bumper element 48 can also include first and second spacer elements 66, 68 positioned adjacent respective ones of the ends 60, 62. Spacer elements 66, 68 can include axial passages 67, 69, respectively, to receive connecting element 50 therethrough with ends 54, 56 extending axially therefrom. Spacer elements 66, 68 can be separate components from body 58 to allow the length and/or angulation of the ends of bumper element 48 relative to longitudinal axis L to be adjusted.

Bone anchor 44 can include an elongated shaft 70 extending distally from a proximal head 72. Shaft 70 can be threaded as shown, or can be in the form of a hook or other suitable bone engaging structure. Shaft 70 is shown fixed relative to head 72, but can also be pivotal relative to head 72 to allow adjustment in the angular orientation of shaft 70 relative to head 72. Head 72 can define a passage 74 for receiving connecting element 50 therein. Passage 74 is located between first and second arms 76, 78, which extend proximally from a lower base portion 80. Passage 74 can define a U-shape or any other suitable shape. Arms 76, 78 can be internally threaded to threadingly receive an engagement member 82.

Engagement member 82 can include a proximal tool engaging portion 84 and a distal shaft portion 86. Shaft portion 86 can be in the form of a set screw to engage arms 76, 78. Tool engaging portion 84 can be severable from shaft 86 upon application of a threshold torque to portion 84 relative to portion 86. Other forms for engagement member 82 are contemplated, including nuts, caps, plugs, and sliding locking elements, for example. In the illustrated embodiment, engagement member 82 can be threaded into passage 74 and into contact with connecting element 50 to secure it in position in head 72. When secured in head 72, connecting element 50 is fixed in position and translation along longitudinal axis L relative to anchor 44 or pivoting relative to anchor 44 is prevented or minimized.

Bone anchor 46 includes a distal shaft 88 extending distally from proximal head 90. Shaft 88 can be threaded as shown, or can be in the form of a hook or other suitable bone engaging structure. Proximal head 90 includes a ring-like shape with a pivotal coupling element 92 pivotally captured therein. Coupling element 92 has a ball-like or spherical shape and defines a passage 94 for receiving and slidable capturing end 56 of connecting element 50 therethrough. The engagement relationship of coupling element 92 with connecting element 50 allows connecting element 50 to axially translate relative to anchor 46, as indicated by arrow 96 in FIGS. 2 and 3. In addition, coupling element 92 can universally pivot to at least some degree about connecting element 50 in response to movement of the vertebral body to which anchor 46 is engaged, as indicated by arrows 98. Accordingly, construct 40 provides a limited range of motion for the vertebrae to which it is engaged to move relative to one another, while providing limits to this motion when coupling element 92 contacts connecting element 50. Undesired movement, such as slippage or displacement of the vertebrae in the axial plane of the spinal column as indicated by arrow 97, is resisted by each of the anchors 44, 46.

In FIG. 5 there is shown another embodiment to bumper element 48 designated as bumper element 48'. Bumper element 48' can be identical to bumper element 48, but includes holes 49 extending through body 58' in communication with passage 64. Bumper element 49' can be made from a polymer material, such as PEEK, or other suitable material. Holes 49 provide increased flexibility and compressibility. Any of the bumper embodiments could be made from PEEK or other polymer material, silicone material, polyurethane, elastomers, or other material providing the desired load resistance properties. In yet another form, the body of the bumper element can be made from a more rigid material, and the ends of the body or spacer elements at the end of the body can be made from a flexible material to allow some compression and thus limited movement of the vertebrae along the axis of the construct.

Referring now to FIGS. 6 and 7, there is shown another embodiment of stabilization construct 20 designated as stabilization construct 110. Several elements in stabilization construct 110 can be similar or identical to those discussed above with respect to construct 40, and thus are designated with the same reference numerals. Stabilization construct 110 includes connector assembly 112 extending between and engaged to first and second anchors 44a, 44b. Anchors 44a, 44b can be identical to anchor 44 discussed above, and are designate as "a" and "b" to indicate the anchors are separate anchors.

Stabilization construct 110 includes a connecting element 114 extending through bumper element 48. Connecting element 114 is positioned in passages 74a, 74b of anchors 44a, 44b and engaged therein with respective ones of the engagement members 130a, 130b. Bumper element 48 and optional spacer elements 66, 68 are positioned between heads 72a, 72b of anchors 44a, 44b in abutting engagement therewith.

Connecting element 114 can include an elongated body 116 extending between opposite ends 118, 120. Ends 118, 120 can include an enlarged, ball-like or spherical shaped extending outwardly from body 116. When secured to anchors 44a, 44b, ends 118, 120 are located axially adjacent to the respective head 72a, 72b on the side thereof opposite the respective adjacent end of bumper element 48. Engagement members 130a, 130b can be engaged to respective ones of the heads 72a, 72b to capture connecting element 116 in the respective passages 74a, 74b while permitting axial movement of connecting element 114 and rotation of connecting element 114 in passages 74a, 74b.

FIG. 8 shows a sectional view of head 72a, 72b of anchor 44a, 44b with connecting element 116 in passage 74a, 74b. Engagement member 130a, 130b can be similar to engagement member 82 discussed above, and can include a distal threaded shaft portion 134 and a proximal tool engaging portion 136. Distal portion 134 can engage head 72a, 72b in passage 74a, 74b. However, proximal portion 136 contact head 72a, 72b to limit advancement of distal portion 134 into passage 74a, 74b. When proximal portion 136 contacts heads 72a, 72b, distal end 132 of shaft portion 134 is spaced from body 116 of connecting element 114 by a gap 122. Accordingly, engagement members 130a, 130b capture connecting element 114 in the anchors 44a, 44b but allow axial movement and rotation of the connecting element 114 and the anchors 44a, 44b relative to one another.

Body 116 of connecting element 114 can axially translate in passages 74a, 74b to allow movement of heads 72a, 72b toward one another and away from one another in response to spinal motion, as indicated by arrow 96 in FIG. 9. For example, as shown in FIG. 6, bumper element 48 can be compressed so that it is bulging radially outwardly in response to movement of heads 72a, 72b toward one another, limiting movement of heads 72a, 72b and thus the adjacent vertebrae toward one another along axis L. Ends 118, 120 also contact heads 72a, 72b in response to movement of heads 72a, 72b away from one another, and thus limit movement of the adjacent vertebrae away from one another along axis L. In addition, anchors 44a, 44b can rotate and pivot relative to connecting element 114 at least until such rotation or pivoting is limited by contact between the anchor and the connecting element. Such translational, rotational and pivoting movement, indicated by arrows 98a and 98b in FIG. 9, allows at least limited motion of the vertebrae to which stabilization construct 110 is engaged while providing limits to that motion. Undesired movement, such as translation of the vertebrae in the axial plane of the spinal column, as indicated by arrow 97, is prevented by contact between the connecting element and respective anchors and engagement members.

FIGS. 10 and 11 shown loading of bumper element 48 in response to spinal extension and flexion, respectively, when stabilization construct 110 is engaged to the pedicles of adjacent lumbar vertebrae, for example. In FIG. 10, extension movement of the posteriorly stabilized vertebrae results in shafts 70a, 70b pivoting away from one another as indicated by arrow 137, pivoting the proximal ends of heads 72a, 72b toward one another about connecting element 114 and into active engagement with the proximal side 48a of bumper element 48. This displacement of heads 72a, 72b and thus the extension of the vertebrae is dynamically resisted by compression of bumper element 48 along proximal side 48a as indicated by arrows 128. The compression loading is greatest along the outermost portion of bumper element 48 and tapers toward longitudinal axis L and connecting element 114.

In FIG. 11, flexion movement of the posteriorly stabilized vertebrae results in shafts 70a, 70b pivoting toward one another as indicated by arrow 138, pivoting the proximal ends of heads 72a, 72b away from one another about connecting element 114 so that the distal sides of heads 72a, 72b actively engage the distal side 48b of bumper element 48. This displacement of heads 72a, 72b and thus the flexion of the vertebrae is dynamically resisted by compression of bumper element 48 along distal side 48b as indicated by arrows 129. The compression loading is greatest along the outermost portion of bumper element 48 and tapers toward longitudinal axis L and connecting element 114.

In FIG. 12 there is shown a lordotic version of stabilization construct 110 designated as stabilization construct 140. Stabilization construct 140 can include several components that are identical to those of stabilization construct 110, and like components are designated with the same reference numerals. In FIG. 12, anchors 44a, 44b are oriented along axes 45a, 45b, respectively. Axes 45a, 45b and thus anchors 44a, 44b are oriented to converge proximally at an angle A1. Connector assembly 142 includes connecting element 114 as discussed above and a bumper element 148 extending about connecting element 114 between heads 72a, 72b. Bumper element 148 includes a body 150 extending between ends 152, 154. Bumper element 148 can further include optional spacer elements 156, 158 adjacent respective one of the ends 152, 154.

The ends of the bumper element 148, whether defined by body 150 or spacer elements 156, 158, can be obliquely oriented to longitudinal axis L so as to extend generally parallel with axes 45a, 45b and thus abuttingly contact heads 72a, 72b. This provides the full surface area at the ends of the bumper element 148 normally in contact with heads 72a, 72b. Resistance to both spinal extension and flexion of the vertebrae to which stabilization construct 140 is engaged is thus provided by bumper element 148 even when the axes of anchors 44a, 44b are not parallel with one another.

FIG. 13 shows a multi-level version of stabilization construct 110 designated as multi-level construct 340. Construct 340 includes an elongated connecting element 342 having a length to extend along at least three vertebrae V and anchors 344, 346, 348 engaged to respective ones of the vertebrae V. Bumper elements 350, 352 are positioned about connecting element 342 and between respective pairs of the anchors 344, 346, 348. Connecting element 342 can be slidably and rotatably captured in each of the anchors 344, 346, 348 with a respective one of the engagement elements 354, 356, 358. Alternatively, connecting element 342 can be rigidly engaged to one or more of the anchors 344, 346, 348.

Figure 14:
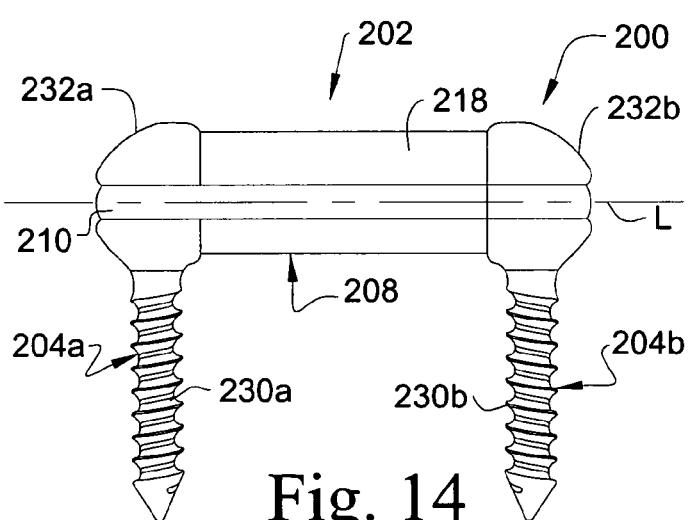
FIG. 14 is an elevation view of another embodiment of the dynamic stabilization construct of FIG. 1.
Figure 15:
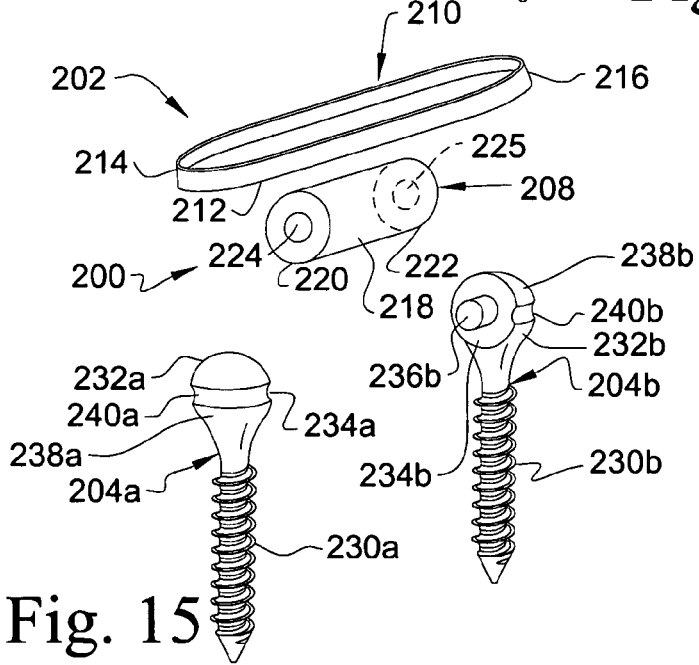
FIG. 15 is an exploded perspective view of the stabilization construct of FIG. 14.

Referring now to FIGS. 14 and 15, there is shown another embodiment of stabilization construct 20 designated as stabilization construct 200. Stabilization construct 200 includes a connector assembly 202 extending between and engageable to a first anchor 204a and a second anchor 204b. Connector assembly 202 includes a bumper element 208 positioned between and abuttingly engaging anchors 204a, 204b and a connecting element 210 extending between and engaged to anchors 204, 206. Bumper element 208 and connecting element 210 extend along longitudinal axis L.

Connecting element 210 include an elongated band-like body 212 extending between a first end 214 and an opposite second end 216. Body 212 can be made from metal or metal alloy such that it provides little or no stretching capability under normal spinal loading. Alternatively, body 212 can be made from a flexible, resilient and elastic material that allows stretching movement of the anchors 204a, 204b and thus the vertebrae to which construct 200 is engaged.

Bumper element 208 includes an elongated cylindrical body 218 extending between a first end 220 and an opposite second end 222 along longitudinal axis L. Body 218 can define central recesses 224, 225 sized and shaped to receive a portion of the respective anchor 204, 206 therein as discussed further below. Recesses 224, 225 can have a blind end in body 218. In another embodiment, recesses 224, 225 are connected by a central passage extending axially through body 218. Cylindrical body 218 can define a circular cross-section as shown, or may include any suitable non-circular cross-sectional shape along all or a portion of the length thereof.

Bone anchors 204a, 204b can be a mirror image of one another when implanted. Each includes an elongated shaft 230a, 230b extending distally from a proximal head 232a, 232b. Shaft 230a, 230b can be threaded as shown, or can be in the form of a hook or other suitable bone engaging structure. Shaft 230a, 230b is shown fixed relative to head 232a, 232b but can also be pivotal relative to head 232a, 232b to allow adjustment in the angular orientation of shaft 230a, 230b relative to head 232a, 232b. Head 232a, 232b includes an inner surface 234a, 234b having a projection 236a (FIG. 20A), 236b extending therefrom along longitudinal axis L. The opposite, outer surface 238a, 238b of head 232a, 232b includes a groove 240a, 240b extending about the head 232a, 232b and in the direction of longitudinal axis L.

When assembled, bumper element 208 is positioned between inner surfaces 234a, 234b of heads 232a, 232b. Projections 236a, 236b can be positioned in respective ones of the recesses 224, 225 of bumper element 208 to resist or prevent slippage from between heads 232a, 232b. Connecting element 210 is positioned in grooves 240a, 240b and around heads 232a, 232b and bumper element 208. Since connecting element 210 extends around outer surfaces 238a, 238b, it couples the heads 232a, 232b to one another and can resist or prevent movement of the heads 232a, 232b away from one another along axis L. Connecting element 210 can further secure bumper element 208 in position between heads 232a, 232b by compressing or maintaining compression of the heads 232a, 232b against bumper element 208.

Stabilization construct 200 can be assembled to provide varying degrees of motion of the vertebrae to which construct 200 is attached. For example, heads 232a, 232b can be compressed toward one another to tightly grip bumper element 208 therebetween, and then connecting element 210 secured around heads 232a, 232b to maintain the applied compression. Connecting element 210 can be relatively inelastic under spinal loading, preventing motion movement of the anchor heads 232a, 232b away from one another and the compressed bumper element 208 prevents movement of anchor heads 232a, 232b toward one another. Alternatively, bumper element 208 can be rigid and relatively incompressible under spinal loading to prevent movement of heads 232a, 232b toward one another.

In another form shown in FIG. 16, connecting element 210 can be elastic under spinal loading and stretch when engaged about heads 232a, 232b to permit at least limited movement of heads 232a, 232b away from one another along longitudinal axis L, as indicated by arrow 96. Bumper element 208 can be compressible under spinal loading to permit movement of the anchor heads 232a, 232b toward one another in response to movement of the vertebrae along longitudinal axis L as also indicated by arrow 96. Furthermore, compressibility of bumper element 208 in response to spinal loading can permit pivoting and rotational movement of the vertebrae relative to one another, as indicated by arrows 98a, 98b.

FIGS. 17 and 18 show loading of bumper element 208 in response to spinal extension and flexion, respectively, when stabilization construct 200 is engaged to the pedicles of adjacent lumbar vertebrae, for example. In FIG. 17, extension movement of the posteriorly stabilized vertebrae results in shafts 230a, 230b pivoting away from one another as indicated by arrow 246, pivoting the proximal ends of heads 232a, 232b toward one another in active engagement with ends 220, 222 of bumper element 208 adjacent proximal side 208a. This displacement of the heads 232a, 232b and thus the extension of the vertebrae is dynamically resisted by compression of bumper element 208 along proximal side 208a as indicated by arrows 250. The compression loading is greatest along the outermost portion of bumper element 208 and tapers toward longitudinal axis L.

In FIG. 18, flexion movement of the posteriorly stabilized vertebrae results in shafts 230a, 230b pivoting toward one another as indicated by arrow 248, pivoting the proximal ends of heads 232a, 232b away from one another so that the outer surfaces 238a, 238b tension connecting element 210 and inner surfaces 234a, 234b contact the respective ends 220, 2222 to compress the distal side 208b of bumper element 208. This displacement of the heads 232a, 232b and thus the flexion of the vertebrae is dynamically resisted by compression of bumper element 208 along distal side 208b as indicated by arrows 252. The compression loading is greatest along the outermost portion of bumper element 208 and tapers toward longitudinal axis L.

In FIG. 19 there is shown a lordotic version of stabilization construct 200 designated as stabilization construct 260. Stabilization construct 260 can include several components that are identical to those of stabilization construct 200, and like components are designated with the same reference numerals. In FIG. 19, anchors 204a, 204b are oriented along axes 205a, 205b, respectively. Axes 205a, 205b and thus anchors 204a, 204b are oriented to converge proximally at an angle A1. Connector assembly 262 includes connecting element 210 as discussed above and a bumper element 268 extending between heads 232a, 232b with connecting element 210 positioned thereabout. Bumper element 268 includes a body 270 extending between ends 272, 274.

Inner surfaces 234a, 234b can be angled relative to axes 205a, 205b so that when anchors 204a, 204b are oriented along axes 205a, 205b inner surfaces 234a, 234b are orthogonal to longitudinal axis L to contact similarly oriented ends 272, 274 of body 270. in another arrangement, ends 272, 274 can be obliquely oriented to longitudinal axis L to contact similarly oriented inner surfaces 234a, 234b so that the surface area at the ends of the bumper element 268 is fully in contact with heads 232a, 232b. Resistance to both spinal extension and flexion movement of the vertebrae to which stabilization construct 260 is engaged is thus provided by bumper element 268 even when the axes of anchors 204a, 204b are not parallel with one another.

Referring now to FIGS. 20A-20E, a method for assembling stabilization construct 200 will be discussed. In FIG. 20A, anchors 204a, 204b are engaged to respective ones of first and second vertebrae. The distance X between inner surfaces 234a, 234b is measured. In FIG. 20B a bumper element 208 having length X+Y between ends 220, 222 is selected. The distance Y is selected to provide a desired tension in connecting element 210. In FIG. 20C, anchors 204a, 204b are distracted to separate heads 232a, 232b. The selected bumper element 208 is positioned between heads 232a, 232b so that projections 236a, 236b can be positioned in respective ones of the recesses 224, 225 of bumper element 208.

In FIG. 20D, anchor heads 232a, 232b are compressed toward one another to bring inner surfaces 234a, 234b in contact with the respective ends 220, 222 and to accommodate placement of connecting element 210 about heads 232a, 232b in grooves 240a, 240b. In the compressed state, bumper element 208 can bulge or flex outwardly. When connecting element 210 is in position, anchor compression can be released and bumper element 208 pushes heads 232a, 232b apart to tension connecting element 210, maintaining the construct in an assembled condition. The distraction provided by bumper element 208 can correspond to or be a function of the length increase Y determined in FIG. 20B.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A spinal stabilization construct, comprising:
   first and second anchors, said first and second anchors each including a proximal head and a distal portion engageable to respective ones of first and second vertebral bodies, wherein said head of said second anchor includes a coupling element defining a passage therethrough;
   a connector assembly extending along a longitudinal axis between said proximal heads of said first and second anchors, said connector assembly including:
      an elongated connecting element including a rigid body extending between opposites ends in a passage through said head of said first anchor and through said passage of said coupling element of said second anchor, wherein said rigid body of said connecting element is configured so that when subjected to spinal column loading said rigid body retains its shape and length;
      a flexible bumper element positioned about said connecting element, said bumper element extending between opposite ends thereof in abutting engagement with said proximal heads and said bumper element compresses in response to and to dynamically resist movement of said heads toward one another; and
      an engagement member coupled to said proximal head of said first anchor, said engagement member securing said respective opposite end of said connecting element in said passage of said proximal head of said first anchor, wherein the other of said opposite ends of said connecting element is captured in said passage of said coupling element of said second anchor and is configured with said proximal head so that said connecting element moves along said longitudinal axis relative to said second anchor and said coupling element is engaged with one of said opposite ends of said bumper element and pivots about said connecting element in response to movement of the first and second vertebrae along the longitudinal axis, and further wherein said coupling element pivots about said connecting element to contact said connecting element to limit movement of the second vertebra relative to the first vertebra.

2. The construct of claim 1, wherein said coupling element in said head of said second anchor is a ball member defining said passage thereof, said ball member being pivotally captured in said proximal head.

3. The construct of claim 1, wherein said engagement member fixes said connecting element in position relative to said first anchor in said passage of said first anchor.

4. The construct of claim 1, wherein said bumper element defines a longitudinal passage extending therethrough for receiving said connecting element.

5. The construct of claim 4, wherein said bumper element includes a number of holes extending through a body thereof in communication with said passage of said bumper element.

6. The construct of claim 5, wherein said body of said bumper element is made from PEEK material.

7. The construct of claim 6, wherein said bumper element includes first and second compressible spacer elements at opposite ends of said body positioned between said body and a respective one of said proximal heads of said first and second anchors.

8. The construct of claim 1, wherein said bumper element includes first and second compressible spacer elements at opposite ends of an elongated body of said bumper element, said spacer elements being positioned between respective ones of said opposite ends and an adjacent one of said proximal heads of said first and second anchors.

9. The construct of claim 8, wherein said connecting element extends through axial passages of said first and second spacer elements.

10. The construct of claim 1, wherein said distal portions of said first and second bone anchors each include a threaded shaft and said proximal head is fixed relative to said shaft, wherein said bumper element compresses in response to displacement of said first and second anchors during flexion and extension of the first and second vertebral bodies when the stabilization construct is engaged thereto.

11. The construct of claim 10, wherein said proximal head of said first anchor includes a base portion at a proximal end of said threaded shaft and a pair of arms extending proximally from said base portion, said pair of arms defining said passage of said first anchor.

12. A method for assembling a spinal stabilization construct, comprising:
   engaging a first anchor to a first vertebra;
   engaging a second anchor to a second vertebra;
   positioning a bumper element around an elongated connecting element with the connecting element extending axially between the first and second anchors along a longitudinal axis and with the bumper element in abutting engagement with the first anchor;
   fixing a first end of the connecting element to the first anchor;
   slidably capturing the second end of the connecting element in a pivoting coupling element of the second anchor with the bumper element extending between the first and second anchors and with the bumper element in engagement with the coupling element so that the second end of the connecting element moves axially relative to the second anchor in response to movement of the first and second vertebrae and the coupling element pivots about the connecting element in response to movement of the first and second vertebrae; and
   compressing the bumper element against the first and second anchors in response to displacement of the first and second anchors during flexion and extension movement of the first and second vertebrae while retaining a shape and length of the connecting element during the flexion and extension movement, and further wherein the coupling element pivots about the connecting element to contact the connecting element to limit movement of the second vertebra relative to the first vertebra.

13. The method of claim 12, further comprising axially restraining movement of the anchors toward one another by contacting the first and second anchors with an adjacent end of the bumper element.

14. The method of claim 12, wherein said coupling element is a ball member pivotally captured in a proximal head of the second anchor.

15. The method of claim 14, wherein engaging the first end of the connecting element includes rigidly engaging the first end of the connecting element to the first anchor.

16. A spinal stabilization construct, comprising:
first and second bone anchors and an elongated connecting element extending between said first and second bone anchors and a bumper element positioned around said connecting element, wherein said bumper element includes opposite first and second ends with said first end positioned in abutting engagement with said first anchor and said bumper element compresses in response to displacement of said first and second anchors during flexion and extension of first and second vertebrae when the stabilization construct is engaged thereto, wherein said connecting element includes a first end extending from said bumper element fixedly engaged with said first anchor and a second end extending from said bumper element and through a coupling element pivotally captured in a proximal head of said second bone anchor with said second end of said bumper element positioned in engagement with said coupling element so that said second bone anchor is movable to translate along said connecting element while said coupling element pivots about said connecting element during flexion and extension of the first and second vertebrae, and further wherein said coupling element pivots about said connecting element to contact said connecting element to limit movement of the second vertebra relative to the first vertebra when said stabilization construct is engaged thereto.

17. The construct of claim 16, wherein said connecting element is rigid so that when subjected to flexion and extension of the first and second vertebrae said connecting element retains its shape and length.

* * * * *